(12) United States Patent
Hansell et al.

(10) Patent No.: US 10,245,153 B2
(45) Date of Patent: Apr. 2, 2019

(54) ARTIFICIAL DISCS (71) Applicant: GLOBUS MEDICAL, INC., Audubon, PA (US)

(72) Inventors: Noah Hansell, King of Prussia, PA (US); Edward Dwyer, Pittsgrove, NJ (US); Jeff Bennett, Pottstown, PA (US)

(73) Assignee: GLOBUS MEDICAL, INC., Audubon, PA (US)

(*) Notice: Subject to any disclaimer, the term of this patent is extended or adjusted under 35 U.S.C. 154(b) by 0 days.

(21) Appl. No.: 14/830,146

(22) Filed: Aug. 19, 2015

(65) Prior Publication Data
US 2015/0351926 A1 Dec. 10, 2015

Related U.S. Application Data (63) Continuation of application No. 14/670,884, filed on Mar. 27, 2015, now Pat. No. 9,144,504, which is a continuation of application No. 13/281,786, filed on Oct. 26, 2011, now Pat. No. 9,017,410.

(51) Int. Cl.
A61F 2/44 (2006.01)
A61F 2/46 (2006.01)
A61F 2/30 (2006.01)

(52) U.S. Cl.
CPC ............ *A61F 2/442* (2013.01); *A61F 2/4425* (2013.01); *A61F 2/4611* (2013.01); *A61F 2002/30014* (2013.01); *A61F 2002/30069* (2013.01); *A61F 2002/3098* (2013.01); *A61F 2002/30166* (2013.01); *A61F 2002/30337* (2013.01); *A61F 2002/30469* (2013.01); *A61F 2002/30504* (2013.01); *A61F 2002/30607* (2013.01);

(Continued)

(58) Field of Classification Search
CPC .......... A61F 2310/00179; A61F 2/4425; A61F 2002/30649; A61F 2002/30014; A61F 2002/30795; A61F 2002/30655; A61F 2002/30902; A61F 2002/30166; A61F 2/4611; A61F 2002/443; A61F 2002/30884
USPC ........................................... 623/17.11–17.16
See application file for complete search history.

(56) References Cited

U.S. PATENT DOCUMENTS

5,401,269 A * 3/1995 Buttner-Janz ......... A61F 2/4425
606/247
5,888,223 A 3/1999 Bray, Jr.
(Continued)

*Primary Examiner* — Eric S Gibson
*Assistant Examiner* — Marcela I Shirsat (57) ABSTRACT A four-component artificial intervertebral disc may provide six degrees of movement: flexion, extension, lateral bending, axial rotation, axial deflection, and anterior/posterior translation. The disc may include a superior endplate, a superior core, an inferior core, and an inferior endplate. The superior endplate may include a concave mating surface, and the inferior endplate may include a spherical mating surface. The superior endplate may roll across the superior core to provide flexion, extension, and lateral bending. The superior endplate may twist or rotate atop the superior core to provide axial rotation, and the superior endplate may slide over the superior core to provide anterior/posterior translation. The superior core may be connected to the inferior core, and the inferior core may be connected to the inferior endplate. The inferior core may be made from a flexible material that may enable the artificial disc to expand or compress vertically.

16 Claims, 7 Drawing Sheets (52) U.S. Cl.
CPC ............... *A61F 2002/30616* (2013.01); *A61F 2002/30647* (2013.01); *A61F 2002/30649* (2013.01); *A61F 2002/30654* (2013.01); *A61F 2002/30655* (2013.01); *A61F 2002/30795* (2013.01); *A61F 2002/30808* (2013.01); *A61F 2002/30878* (2013.01); *A61F 2002/30884* (2013.01); *A61F 2002/30902* (2013.01); *A61F 2002/30904* (2013.01); *A61F 2002/443* (2013.01); *A61F 2310/00023* (2013.01); *A61F 2310/00029* (2013.01); *A61F 2310/00179* (2013.01); *A61F 2310/00407* (2013.01); *A61F 2310/00796* (2013.01)

(56) References Cited

U.S. PATENT DOCUMENTS

| | | | |
|---|---|---|---|
| 7,083,651 B2 * | 8/2006 | Diaz | A61F 2/4425 623/17.13 |
| 7,250,060 B2 | 7/2007 | Trieu | |
| 7,503,935 B2 * | 3/2009 | Zucherman | A61B 17/1671 623/17.11 |
| 9,017,410 B2 | 4/2015 | Hansell et al. | |
| 2004/0117022 A1 * | 6/2004 | Marnay | A61F 2/4425 623/17.16 |
| 2004/0143332 A1 | 7/2004 | Krueger et al. | |
| 2004/0158254 A1 * | 8/2004 | Eisermann | A61B 17/1642 606/79 |
| 2005/0033431 A1 * | 2/2005 | Gordon | A61B 17/7032 623/17.11 |
| 2005/0085917 A1 * | 4/2005 | Marnay | A61F 2/4425 623/17.16 |
| 2006/0025862 A1 * | 2/2006 | Villiers | A61F 2/4425 623/17.14 |
| 2007/0100454 A1 | 5/2007 | Burgess et al. | |
| 2009/0054986 A1 * | 2/2009 | Cordaro | A61F 2/4425 623/17.15 |
| 2010/0217395 A1 * | 8/2010 | Bertagnoli | A61B 17/14 623/17.16 |

* cited by examiner

ARTIFICIAL DISCS

CROSS REFERENCE TO RELATED APPLICATIONS

This patent application is a continuation of U.S. patent application Ser. No. 14/670,884 filed on Mar. 27, 2015 which is a continuation of U.S. Pat. No. 9,017,410 filed on Oct. 26, 2011, which is incorporated in its entirety herein.

BACKGROUND OF THE DISCLOSURE

1. Field of the Disclosure

The disclosure is directed to a device for replacing a diseased or damaged intervertebral disc. In particular, the device provides a wider range of motion than alternative treatment options, such as, for example, a spinal fusion. Specifically, the device may allow three or more degrees of freedom or different types of movement.

2. Related Art

The spine is composed of several individual bones, known as vertebrae. The vertebrae vary in size, shape, and function in different regions of the spine. The cervical vertebrae make up the bones of the neck and provide for much of the movement of the head. The thoracic vertebrae act as anchors for the ribs and are relatively immobile. The lumbar vertebrae, located at the base of the spine, are the largest vertebrae and allow movement and articulation of the trunk.

In between each pair of vertebrae is an intervertebral disc, which consists of a fibrous outer portion and a gelatinous inner portion. The discs allow the vertebrae to move and articulate relative to one another. They also act as a shock absorber when there is a blow to the spine, such as from a fall or a strike on the head. In particular, an intervertebral disc is capable of at least six different motions or degrees of freedom: flexion, which is bending forward from the waist; extension, which is bending backward from the waist; lateral bending, or leaning sideways; axial rotation, which is turning or twisting to one side or the other; axial deflection, which may also be known as axial compression, vertical extension, or compression along the spine; and anterior/posterior (A/P) translation, which is when one vertebrae slides forward or backward relative to a neighbor without changing its angle relative to the neighboring vertebra.

The intervertebral disc can be injured as a result of aging, trauma, or disease. The disc can become desiccated or otherwise lose or weaken in structure, a condition known as degenerative disc disorder (DDD). A herniated disc is one that has developed a tear in the outer portion, allowing the inner portion to push out. In any case, a damaged disc no longer permits movement as it once did. As the vertebrae move out of their normal, healthy position, the patient may develop chronic, and in some case debilitating, pain as nerves are compressed.

Historically, the injured disc, in a condition such as DDD or herniated disc, can be treated with spinal fusion. Spinal fusion can also be indicated as a treatment for tumors, fractures, and conditions such as scoliosis and kyphosis. In the fusion procedure, a discectomy is performed to remove the damaged disc and the adjacent vertebrae are physically joined together with rods, wire, or other instrumentation. A bone graft is placed between the vertebrae, and over several months, the vertebrae grow together. A typical fusion patient does not notice any loss in mobility because her range of motion was even more restricted by the original condition or injury.

Nevertheless, the lack of motion between the fused vertebrae places increased stress on the surrounding vertebrae and intervertebral discs. This increased stress may lead to premature failure or injury to these components, requiring further treatment. In addition, a fusion procedure may be a major operation, requiring open back surgery and a long recovery period. For these reasons, it is typically a treatment of last resort, reserved for severe cases or when other treatment options have failed.

Alternatives to the open spine fusion procedure, including minimally invasive procedures and artificial disc replacements, are in various stages of development and practice, but these alternatives have yet to see widespread adoption. Minimally invasive procedures involve the use of small incisions, remote control manipulation of instruments, and observation through an endoscope or similar device. These procedures may result in less trauma to the patient and improved recovery times. Minimally invasive surgery can also be used to replace an injured intervertebral disc. Instead of fusing the vertebrae above and below a damaged or diseased disc, the disc can be replaced with an artificial disc. Current discs may provide a greater range of motion than an equivalent fusion procedure while offering equal or better treatment of the condition.

Current artificial discs, however, suffer from one or more drawbacks. Some discs do not enable a full range of motion along all degrees of freedom provided by a natural intervertebral disc. Current discs may not properly restrict motion along a degree of freedom, which may result in hyperextension and injury to the patient. A disc may not be compatible with minimally invasive procedures for replacing the injure disc, or a disc may only be compatible with an anterior procedure. In an anterior procedure, a surgeon accesses the spine through an incision in the abdomen or neck. Alternative routes for accessing the intervertebral disc include: posterior, where the incision is made directly on the patient's spine; transforaminal, where the incision is placed to one side of the spine; and lateral, where the incision is on the patient's flank.

Accordingly, there is a need for an artificial disc that enables all six degrees of movement, restricts movement along one or more degrees, and/or is compatible with a non-anterior surgical procedure.

SUMMARY OF THE DISCLOSURE

The disclosure meets the foregoing need and allows an artificial disc to provide three to six degrees of freedom using, e.g., a four-part design, which results in a more natural range of movement and other advantages apparent from the discussion provided herein.

Accordingly, one aspect of the disclosure describes an artificial disc for replacing a natural intervertebral disc. The artificial disc includes a superior endplate, a superior core, a flexible inferior core, and an inferior endplate. The superior endplate includes a bi-convex superior surface and a concave inferior surface. The superior core includes a convex superior surface configured to contact the concave inferior surface of the superior endplate. The flexible inferior core is connected to the superior core. The inferior endplate is connected to the inferior core and includes a bi-convex inferior surface.

The geometry of the bi-convex superior surface may be selected so as to provide an anatomical fit to an inferior surface of a first vertebral body, and the geometry of the bi-convex inferior surface may be selected so as to provide an anatomical fit to a superior surface of a second vertebral body. The artificial disc may include first multiple serrated keels attached to the superior surface of the superior endplate, as well as second multiple serrated keels attached to the inferior surface of the inferior endplate. The first multiple serrated keel may include one or more holes perpendicular to the longitudinal axis of the keel, and the second multiple serrated keel may likewise include one or more holes perpendicular to the longitudinal axis of the keel. The superior surface of the superior endplate, including the first multiple serrated keels, may be treated with a titanium and/or hydroxyapatite plasma spray coating. Additionally, the inferior surface of the inferior endplate, including the second multiple serrated keels, may be treated with a titanium and/or hydroxyapatite plasma spray coating. The superior endplate, superior core, and inferior core may each be made from one or more of the following: titanium, Cr—Co—Mo (chromium, cobalt, molybdenum) alloy, or polyetheretherketone (PEEK). The inferior core may be made from polycarbonate urethane.

According to another aspect of the disclosure, an artificial disc includes a superior endplate and an inferior endplate. The superior endplate includes a bi-convex superior surface and one or more serrated keels located on the superior surface. The superior endplate also includes both an anterior socket and a posterior socket for connecting to and disconnecting from a holder tool. The inferior endplate includes a bi-convex inferior surface and one or more serrated keels located on the inferior surface. The inferior endplate also includes both an anterior socket and a posterior socket for connecting to and disconnecting from a holder tool.

The superior multiple serrated keels may include one or more holes that are perpendicular to the longitudinal axis of the keels. The inferior multiple serrated keels may similarly include one or more holes that are perpendicular to the longitudinal axis of the keel. The geometry of the bi-convex superior surface may be designed to provide an anatomical fit to an inferior surface of a vertebral body. The superior surface of the superior endplate may include a titanium and/or hydroxyapatite plasma spray coating. The geometry of the bi-convex inferior surface may be designed to provide an anatomical fit to a superior surface of a vertebral body. The inferior surface of the inferior endplate may include a titanium and or hydroxyapatite plasma spray coating.

The superior endplate may include a bi-convex inferior surface, and the inferior endplate may include a biconvex superior surface. The bi-convex inferior surface and the bi-convex superior surface may contact one another and provide a rolling/sliding, convex-on-convex articulation. The superior endplate may be made from titanium, Cr—Co—Mo alloy, ceramic, or PEEK, and the inferior endplate may be made from titanium, Cr—Co—Mo alloy, ceramic, or PEEK.

In another embodiment, the superior endplate may include a center region, one or more side regions, and a lip separating the center region and the side regions. The center region of the superior endplate may have a thicker cross-section than the side region and may include a concave spherical portion located in the center region. The inferior endplate may include a center region, a side region, and a lip separating the center region and the side region. The center region of the inferior endplate may have a thinner cross-section than the side region and may have a mating convex sphere located in the center region. The mating sphere may be structured and arranged to contact the concave spherical portion of the superior endplate when the disc is fully assembled. The superior endplate may be made from titanium, Cr—Co—Mo alloy, ceramic, or PEEK, and the inferior endplate may be made from titanium, Cr—Co—Mo alloy, ceramic, or PEEK.

The artificial disc may also include a first insert and a second insert. Both inserts may be made from PEEK. The first insert may connect to a socket in the superior endplate, and the second insert may connect to a socket in the inferior endplate. The first insert may include a concave mating surface, and the second insert may include a spherical mating surface structured and arranged to connect the mating surface of the first insert. The superior endplate may be made from titanium or Cr—Co—Mo alloy, and the inferior endplate may be made from titanium or Cr—Co—Mo alloy.

In yet another aspect of the disclosure, an artificial disc includes a first endplate, a second endplate, a first insert, and a second insert. The first endplate includes a first rail and a second rail. The second rail is spaced a distance apart from the first rail. The first endplate further includes a body connected to both the first rail and the second rail, and the body includes a socket for receiving an insert. The second endplate is identical to the first. The first insert connects to the socket of the first endplate, and the second insert connects to the socket of the second endplate.

The first insert may include a concave mating surface, and the second insert may include a spherical mating surface. Moreover, the spherical mating surface may be structured and arranged to contact the concave mating surface of the first insert. The first insert and the second insert may be made from PEEK. The first endplate and the second endplate may be made from titanium or Cr—Co—Mo alloy.

Additional features, advantages, and embodiments of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings:

FIGS. 4A-4D show various views of a superior endplate of an artificial disc, according to an additional aspect of the disclosure;

FIG. 4A provides a superior view of the superior endplate;

FIGS. 5A-5D show various views of an inferior endplate of the artificial disc of FIGS. 4A-D;

FIG. 5A provides an inferior view of the inferior endplate;

DETAILED DESCRIPTION OF THE DISCLOSURE

The embodiments of the disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

According to an aspect of the disclosure, an artificial disc may be capable of providing all six of the six degrees of movement seen in natural intervertebral discs. An example of this type of artificial disc is shown in an exploded view in FIG. 1. Artificial disc 100 may include 4 components: superior endplate 110, superior core 120, inferior core 130, and inferior endplate 140. The superior endplate 110, superior core 120, and inferior endplate 140 may each be made from a rigid, bio-compatible material such as, e.g., titanium or polyetheretherketone (PEEK). Components that contact bone, including the endplates, may be treated with a titanium and/or hydroxyapatite plasma spray coating. This coating may serve to encourage bony on-growth, improving the strength and stability of the connection between the component and the underlying bone. For example, an endplate 110, 140 may be treated with a titanium and/or hydroxyapatite plasma spray coating to foster bony on-growth and strengthen the connection or interface between the endplate 110, 140 and the vertebral body to which it is attached. The inferior core 130 may be made from a polymer, such as, e.g., polycarbonate urethane (PCU), that may allow the disc 100 to be compressed along its vertical axis.

Figure 1:
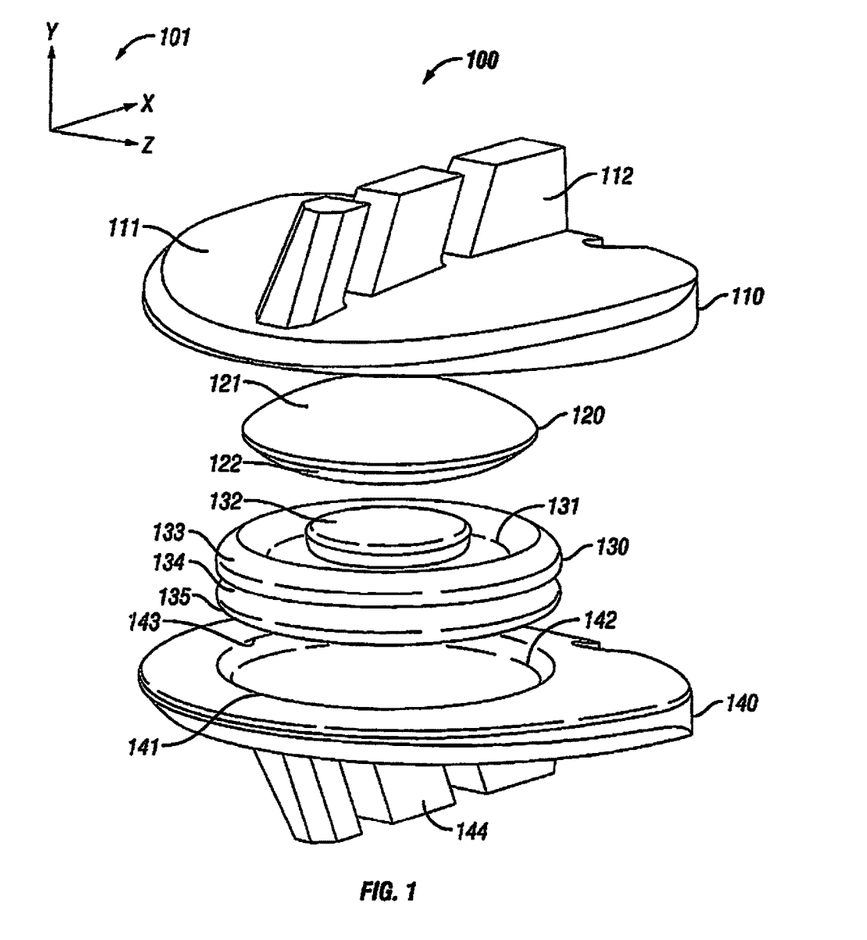
FIG. 1 shows an exploded view of an artificial disc that may provide six degrees of movement, according to one aspect of the disclosure.

Axes 101 may represent the three-dimensional orientation of the artificial disc 100. For example, the axis marked X may be approximately aligned with or parallel to an anterior/posterior axis of the disc 100. The Y axis may be roughly parallel to a superior/inferior axis of the disc 100. This axis may also be somewhat indicative of the vertical axis of the spine, which may be commonly referred to simply as the axis of the spine. The Z axis may be approximately parallel to a lateral axis of the artificial disc 100.

The superior endplate 110 may have an upper or superior surface 111. The superior surface 111 may be bi-convex, i.e. curved from left to right and front to back. This curvature may give the surface 111 a shape akin to a partial dome or sphere. The curvature may be complementary to the natural curvature of an endplate of a vertebral body and may provide for an anatomical fit between the surface 111 and the vertebral body (not shown). One or more serrated keels 112 may be located on superior surface 111. Each keel 112 may have a longitudinal axis that is roughly aligned along an anterior/posterior axis of the disc 100. Once a discectomy has been completed, removing the damaged natural disc, a groove or channel may be cut into the vertebral body (not shown) to receive each keel 112. Each keel 112 may have one more holes (not shown) perpendicular to the longitudinal axis of the keel. These holes provide an aperture for bony in-growth, which may strengthen the connection or interface between the endplate and the vertebral body.

The superior core 120 may have a superior mating surface 121 that is domed or curved. The surface 121 may contact the concave inferior surface 113 of the superior endplate 110, as described below. The superior core 120 may also have an inferior surface 122 that mates with the inferior core 130. The superior core 120 may be made from a hard material suitable for bearing contact, such as, for example, titanium, cobalt-chromium-molybdenum (Co—Cr—Mo) alloy, ceramic, PEEK, or the like.

The inferior core 130 may be generally cylindrical in shape. The superior surface 131 of inferior core 130 may be substantially concave with a mating knob 132 for attaching to the superior core 120, as described below with reference to FIG. 3. The side of inferior core 130 may be divided into an upper side 133 and a lower side 135 by a mating groove 134. The mating groove 134 may help to attach the inferior core 130 to inferior endplate 140.

The inferior endplate 140 may have a mating socket 142 formed in its superior surface 141. The mating socket 142 may include a mating rim 143 that is complementary to the mating groove 134 of the inferior core 130. The mating socket 142 may have an overall shape that is complementary to the lower portion of inferior core 130. The inferior core 130 may fit into and be retained by the mating socket 142. The inferior endplate 140 may additionally have one or more serrated keels 144, similar to that found on the superior endplate 110. The keel 144 may have a longitudinal axis that is roughly aligned along an anterior/posterior axis of the disc 100. The keel 144 may also have one or more holes perpendicular to the longitudinal axis of the keel to encourage bony in-growth, as described above with respect to the superior endplate 110. The inferior endplate 140 may have an inferior surface (not shown) that is bi-convex, as described above with respect to superior surface 111.

Figure 2:
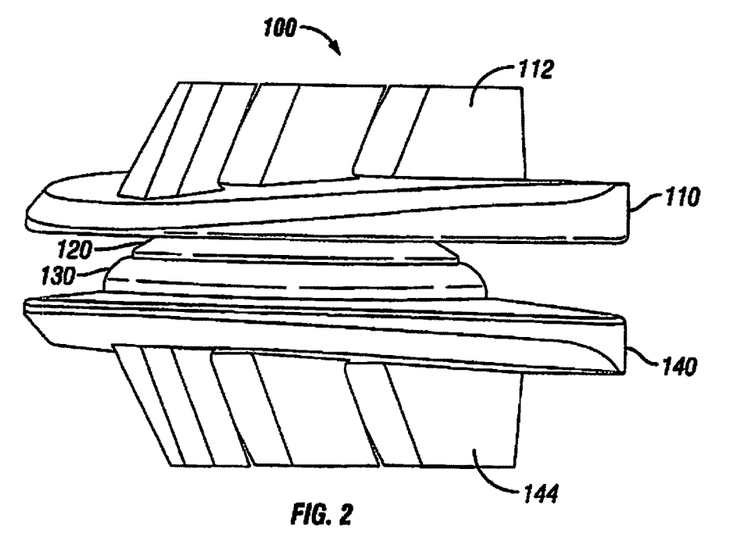
FIG. 2 shows a view of the disc of FIG. 1 in an assembled state.

FIG. 2 illustrates a view of an assembled artificial disc 100. The superior edge of keel 112 may be parallel or roughly parallel to the inferior edge of the keel 144. When fully assembled, the superior endplate 110 and the inferior endplate 140 may be closer together on one side and farther apart on the opposite side. The axis formed by these two points may be aligned or roughly aligned with the anterior/posterior axis of the disc 100, the longitudinal axis of the keel 112, and/or the longitudinal axis of the keel 144. The side of disc 100, where the endplates 110, 140 are closest together may be the posterior end of the disc 100, and the side where the endplates 110, 140 are farthest apart may be the anterior end of the disc 100. Serrations or divisions of the keels 112, 144 may be parallel or approximately parallel to the superior/inferior axis of the disc 100 (i.e. the axis of the spine). Serrations or divisions of the keels 112, 144 may be perpendicular to the respective surface of the superior endplate 110 or inferior endplate 140. Alternatively, the serrations or divisions may be angled with respect to the superior/inferior axis of the disc 100, the axis of the spine, or the surface of the endplates 110, 140. The serrations or divisions may be angled away from the posterior end or side of the artificial disc 100 and toward the anterior end or side. This angle may reduce or prevent the disc 100 from moving toward the anterior, i.e. backing out of the intervertebral space and/or groove(s) cut into vertebral bodies (not shown).

Figure 3:
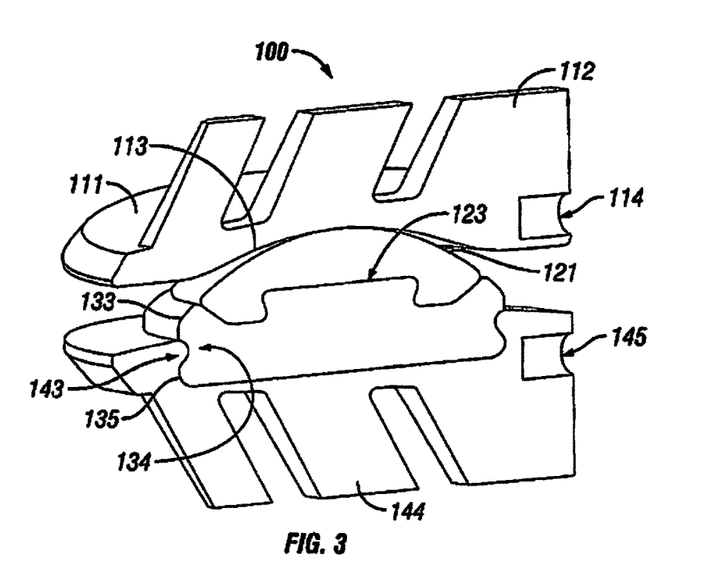
FIG. 3 shows a cutaway view of the assembled disc of FIG. 2.

FIG. 3 provides a cutaway view of the assembled disc 100, revealing the interconnections between the four components of the disc 100. Superior endplate 110 may include a socket 114, and inferior endplate 140 may similar include a socket 145. Sockets 114, 145 may receive a holder or tool to assist a surgeon in grasping the artificial disc 100 and inserting it into an intervertebral space during a surgical procedure.

The inferior surface of superior endplate 110 may include a concave mating surface 113. The mating surface 113 may contact the superior core 120, as shown in FIG. 3. The curved or domed superior mating surface 121 of the superior core 120 may have a smaller radius than the inferior mating surface 113 of the superior endplate 110. This arrangement may be similar to a smaller ball placed within a larger hollow concave sphere or bi-concave channel. The contact area between the two spheres may be reduced to a single point of contact. Similarly, the contact area between the superior endplate 110 and the superior core 120 may be reduced to a very small area, including, e.g., a single point.

The small contact area may permit the artificial disc to provide several degrees of freedom. For example, by configuring the inferior mating surface 113 of the superior endplate into a bi-convex channel, the superior endplate 110 may articulate or roll across the superior core 120 on an anterior/posterior axis to provide for extension and flexion of the spine. Articulation or rolling along a left/right axis may permit lateral bending. Furthermore, the superior endplate 110 may rotate or articulate on top of the superior core 120 to allow axial rotation. In addition, the superior endplate 110 may slide or shift relative to the superior core 120 along an anterior/posterior axis to emulate anterior/posterior translation. In this manner, the connection between the superior endplate 110 and superior core 120 may enable four degrees of movement. In another embodiment of the design, the inferior mating surface 113 of the superior endplate may be configured to additionally allow the superior endplate 110 to slide or shift relative to the superior core 120 along a medial/lateral axis to emulate medial/lateral translation. In this manner, the connection between the superior endplate 110 and superior core 120 may enable five degrees of movement.

The superior core 120 may include an inferior mating surface 122 with a mating socket 123. As shown in FIG. 3, the socket 123 may include one or more angled walls such that the socket 123 is narrower at its inferior end and wider at its superior end. This arrangement may create a rim or lip around the opening of socket 123.

The mating socket 123 may be configured to receive a mating knob 132 on the superior surface 131 of the inferior core 130. The mating knob 132 may have a configuration that is complementary to the mating socket 123. For example, the knob 132 may be wider at its superior end and narrower at its inferior end. The knob 132 and the socket 123 may be designed with such dimensions that, once the components are joined, the connection is permanent and the components cannot be separated. The normal biomechanical forces acting on an intervertebral disc may not be able to separate the superior core 120 and the inferior core 130.

As described above, the inferior core 130 may be made from a polymer that is flexible, at least in comparison to materials such as titanium and PEEK. Polycarbonate urethane (PCU) is one example of a polymer that may be suitable for constructing the inferior core 130. The use of a flexible material for the inferior core 130 may enable the artificial disc 100 to have an additional degree of freedom, axial deflection or axial compression.

To enable six degrees of freedom in movement, the inferior core 130 may be compressed slightly as it is inserted into the intervertebral space. The inferior core 130 may then expand when the patient extends her spine vertically, mimicking the flexibility of a natural intervertebral disc. In addition, the flexible material of the inferior core 130 may allow the artificial disc 100 to be compressed when the patient experience's a spinal compression or deflection. Again, this compression may replicate the behavior of a natural intervertebral disc. The compression of the artificial disc 100 may help cushion the spine and vertebrae against damage and injury when the patient undergoes axial deflection or compression.

The inferior core 130 may be roughly cylindrical in shape with a side that may be roughly straight. Alternatively, the side may be somewhat convex. In either form, the side may be divided into an upper side 133 and a lower side 135 by a mating groove 135. The mating groove 135 may be complementary to a mating rim 143 in a mating socket 142 on the inferior endplate 140. As seen in FIG. 3, the lower wall 135 may be retained within the mating socket 142, while the upper wall 133 may extend above the superior surface 141 of the inferior endplate 140. The structure and arrangement of the mating socket 142, mating rim 143, mating groove 134, and lower wall 135 may create a permanent connection between the inferior core 130 and the inferior endplate 140. The normal biomechanical forces acting on an intervertebral disc may not be able to separate the inferior core 130 and the inferior endplate 140.

The inferior endplate 140 may have a superior surface 141, and the mating socket 142, which may include the mating rim 143, may be formed in the superior surface. The inferior endplate 140 may also have an inferior surface 146. The inferior surface 146 may be bi-convex, i.e. curved from left to right and front to back. This curvature may give the surface 146 a shape akin to a partial dome or sphere. The curvature may be complementary to the natural curvature of an endplate of a vertebral body and may provide for an anatomical fit between the surface 146 and the vertebral body. One or more serrated keels 144 may be located on the inferior surface 146. Each keel 144 may have a longitudinal axis that is roughly aligned along an anterior/posterior axis of the disc 100. Once a discectomy has been completed, a groove may be cut into the vertebral body (not shown) to receive each keel 144. Each keel 144 may have one or more holes (not shown) that are perpendicular to the longitudinal axis of the keel 144. These holes may provide an aperture for bony in-growth, which may strengthen the connection or interface between the endplate and the vertebral body.

The artificial disc 100 may provide the same six degrees of movement found in healthy, natural intervertebral discs: flexion, extension, lateral bending, axial rotation, anterior/posterior translation, medial/lateral translation and axial deflection. The first five degrees of movement may be enabled by the interface between the superior endplate 100 and the superior core 120. This interface may utilize a rolling and articulating sphere-on-sphere design, as described above. The sixth degree of movement, axial deflection, may also be known as axial compression. This type of movement may be enabled by the relatively flexible material used to construct the inferior core 130. The inferior core 130 may be compressed slightly when the artificial disc 100 is inserted in the intervertebral space, which may allow the disc to expand when a patient's spine is lengthened or stretched. In addition, the inferior disc 130 may be further compressed when the patient's spine experiences axial compression or deflection.

Figure 4A:
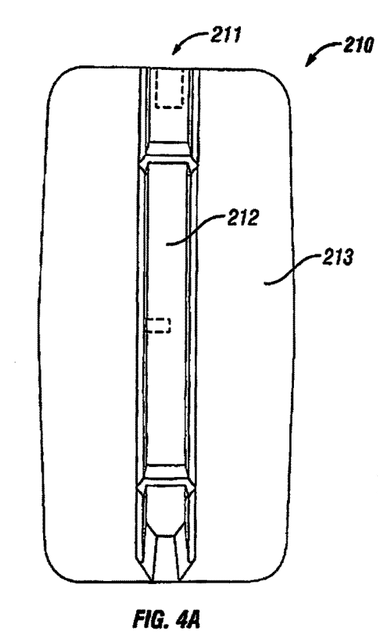
Figure 4B:
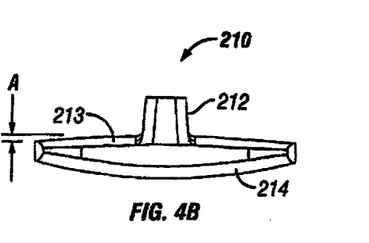
FIG. 4B provides a lateral view of the superior endplate.
Figure 4C:
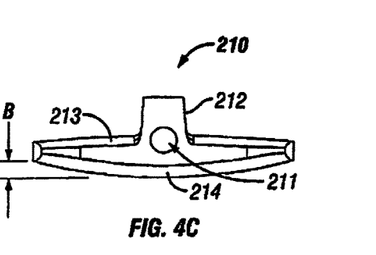
FIG. 4C provides a lateral view of the superior endplate.
Figure 4D:
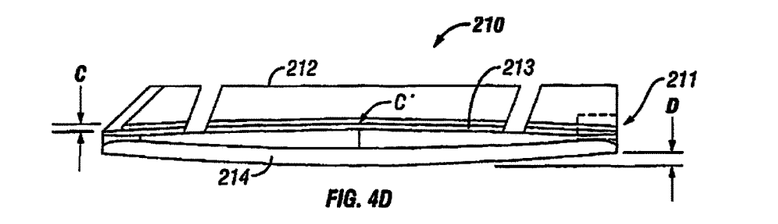
FIG. 4D provides an anterior view of the superior endplate.

FIGS. 4A-4D show the superior endplate 210 of a two-component artificial disc 200 according to an additional aspect of the disclosure. FIGS. 5A-5D show the inferior endplate 220 of the two-component artificial disc 200, and FIG. 6 illustrates how the two endplates 210, 220 may work together. FIG. 4A provides a superior view of the endplate 210. FIG. 4B provides a lateral view of the endplate 210. FIG. 4C provides an opposite lateral view of endplate 210. FIG. 4D provides a anterior view of endplate 210.

The endplate 210 may include one or more serrated keels 212. The keel 212 may have a longitudinal axis that is roughly aligned along an medial/lateral axis of the disc 200, discussed below with respect to FIG. 6. Each keel 212 may have one or more holes (not shown) that are perpendicular to the longitudinal axis of the keel to encourage bony in-growth from the attached vertebral body. The endplate 210 may include a socket 211 for connecting to a holder or tool (not shown) that may be used by a surgeon to insert the disc 200 into a patient's spine. While the socket 211 is shown on the lateral end of the disc 200, the disc 200 may alternatively or additionally include a socket at its anterior and posterior end (not shown).

The endplate 210 may have a superior surface 213 that is bi-convex. An arrow A indicates the anterior/posterior curvature of surface 213, and an arrow C indicates the medial/lateral curvature of the surface 213. (The upper line of arrow C is tangential to the line and at the point indicated by an arrow C'.) The bi-convex shape may be complementary to a vertebral body to which the artificial disc 200 may be attached and may provide for an anatomical fit between the surface 213 and the vertebral body (not shown). The curvature indicated by arrows A and C may vary for different aspects of the disc 200, e.g. discs intended for use in different regions of the spine, or discs intended to replace different natural intervertebral discs.

In addition, the endplate 210 may include an inferior surface 214 that is bi-convex. Thus, the inferior surface 214 may have a shape akin to a portion of a dome or sphere. An arrow B indicates the anterior/posterior curvature of surface 214, and an arrow D shows the medial/lateral curvature of the surface 214.

Figure 5A:
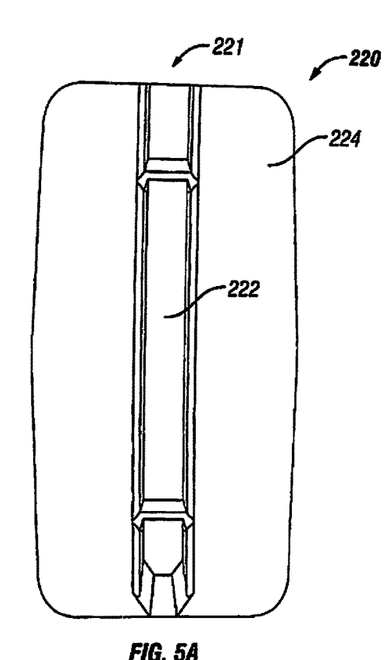
Figure 5B:
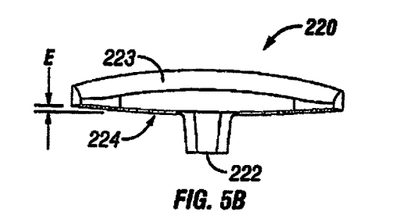
FIG. 5B provides a lateral view of the inferior endplate.
Figure 5C:
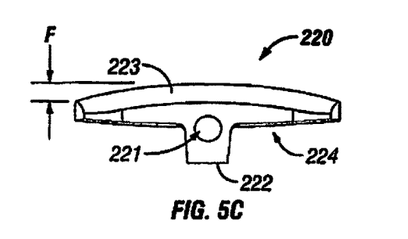
FIG. 5C provides a lateral view of the inferior endplate.
Figure 5D:
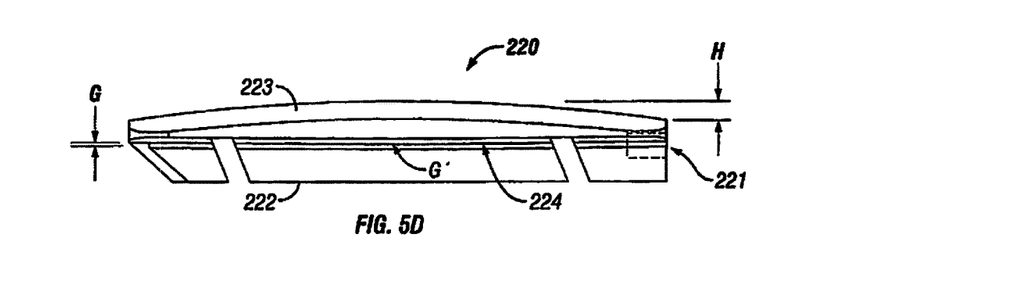
FIG. 5D provides an anterior view of the inferior endplate.
Figure 6:
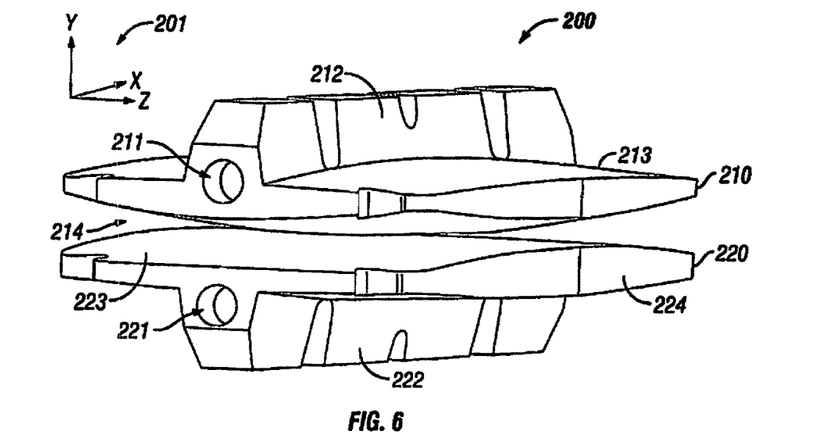
FIG. 6 illustrates how the superior endplate of FIGS. 4A-4D may work together with the inferior endplate of FIGS. 5A-5D.

FIG. 5A provides an inferior view of the endplate 220. FIG. 5B provides a lateral view of endplate 220. FIG. 5C provides an opposite lateral view of endplate 220. FIG. 5D provides an anterior view of endplate 220. The endplate 220 may have an inferior surface 224 with one or more serrated keels 222. Each keel 222 may have a longitudinal axis that is roughly aligned along an medial/lateral axis of the disc 200, discussed below with respect to FIG. 6. The keel 222 may have one or more holes (not shown) that are perpendicular to the longitudinal axis of the keel. The holes may encourage bony in-growth, strengthening the attachment or interface between the endplate 222 and a vertebral endplate (not shown). The endplate 220 may include a socket 221 for connecting to a holder or tool (not shown) that may be used by a surgeon to insert the disc 200 into a patient's spine. While the socket 221 is shown on the lateral end of the disc 200, disc 200 may alternatively or additionally include a socket at its anterior and posterior end (not shown).

The inferior surface 224 may have a bi-convex shape, similar to the superior surface 213 of the superior endplate 210. The anterior/posterior curvature of the inferior surface 224 is indicated by an arrow E in FIG. 5B, and the medial/lateral curvature is indicate by an arrow G in FIG. 5D. (The lower line of the arrow G is tangential to the line and at the point indicated by arrow G'.) The curvature may be complementary to the natural curvature of an endplate of a vertebral body and may provide for an anatomical fit between the surface 224 and the vertebral body (not shown). The curvature of inferior surface 224 may or may not match that of superior surface 213. In particular, the curvature shown at arrow A may be the same as that of arrow E, or the curvature may be different. The curvature indicated at arrow C may be the same as that of arrow G, or the curvature may be different. The curvatures of the inferior surface 224 and the superior surface 213 may vary based upon a number of factors, as will be understood by those skilled in the art. Exemplary factors may include, without limitation, the region of the spine into which the artificial disc is inserted, as well as the specific natural intervertebral disc that is being replaced.

The endplate 220 may have a superior surface 223 with a bi-convex shape, similar to the inferior surface 214 of superior endplate 210. The anterior/posterior curvature is shown by an arrow F in FIG. 5C, and the medial/lateral curvature is shown by an arrow H in FIG. 5D. The curvature of superior surface 223 may or may not be the same as that of inferior surface 214. The curvature indicated by arrow F may be the same as that of arrow B, or it may be different. The curvature indicated by arrow H may be the same as that of arrow D, or it may be different.

FIG. 6 shows an assembled artificial disc 200, including superior endplate 210 and the inferior endplate 220. Axes 201 may represent the three-dimensional orientation of the artificial disc 200. For example, the axis marked X may be approximately aligned with or parallel to an medial/lateral axis of the disc 200. The Y axis may be roughly parallel to a superior/inferior axis of the disc 200. The Z axis may be approximately parallel to a anterior/posterior axis of the artificial disc 200.

The inferior surface 214 of the superior endplate 210 may contact the superior surface 223 of the inferior endplate 220. Since both the inferior surface 214 and the superior surface 223 are bi-convex, the contact area between the endplates 210, 220 may be minimal. This arrangement may allow the endplates 210, 220 to articulate against each other in a rolling/sliding or sphere-on-sphere manner. In particular, the endplates 210, 220 may roll laterally to permit lateral bending, and they may roll along an anterior/posterior axis to enable flexion and extension. In addition, the superior endplate 210 may rotate relative to the inferior endplate 220, or vice versa, to allow axial rotation. It should be noted that sliding between surfaces 214 and 223 may also occur.

The artificial disc 200 may include sockets 211, 221 at both lateral ends, or just at one lateral end. The artificial disc 200 may be made from metal, such as, e.g., stainless steel, titanium, cobalt-chromium-molybdenum (Co—Cr—Mo) alloy, or the like; ceramic; PEEK; or any other hard material suitable for bearing contact, as will be understood by one skilled in the art. Surfaces of the artificial disc 200 that will contact bone, such as the superior surface 213 and the inferior surface 224, may be treated with a titanium and/or hydroxyapatite plasma spray coating to encourage bony on-growth. The bony on-growth may act to strengthen the attachment or interface between the artificial disc 200 and the underlying vertebrae.

Figure 7:
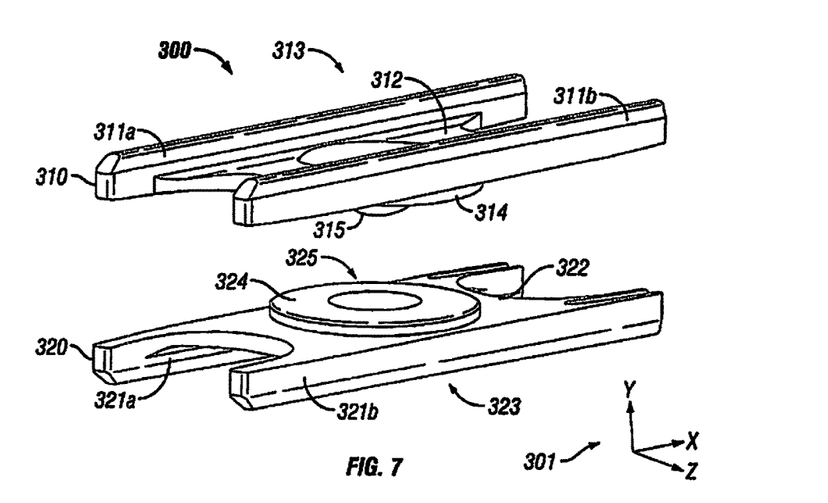
FIG. 7 shows an artificial disc, according to a further aspect of the disclosure.

FIG. 7 shows an artificial disc 300 according to a further aspect of the disclosure. The artificial disc may include a superior endplate 310 and an inferior endplate 320. Each endplate 310, 320 may include a metal component and a polymer insert. The metal components may be identical, so that the superior endplate 310 differs from the inferior endplate 320 only in the polymer insert. The superior endplate 310 may include two rails 311a, 311b that are joined by a body 312, which may have a socket 313 for a polymer insert 314. Likewise, the inferior endplate 320 may include two rails 321a, 321b that are joined by a body 322, which may have a socket 323 for a polymer insert 324.

Axes 301 may represent the three-dimensional orientation of the artificial disc 300. For example, the axis marked X may be approximately aligned with or parallel to an medial/lateral axis of the disc 300. The Y axis may be roughly parallel to a superior/inferior axis of the disc 300. The Z axis may be approximately parallel to a medial/lateral axis of the artificial disc 300.

Following a discectomy, slots or holes may be cut into the endplates of the vertebral bodies (not shown) to receive the rails 311s, 311b, 321a, and 321b. The rails, along with any other part that contacts bone, may be treated by a titanium and/or hydroxyapatite plasma spray coating to encourage bony on-growth. Bony on-growth may enhance the stability of the attachment or interface between the endplate 310, 320 and its associated vertebra.

The endplates 310, 320 may be constructed from titanium, Co—Cr—Mo alloy, or any other metal or alloy, as will be understood by those skilled in the art. Since the endplates 310, 320 may be identical in design, the load of the vertebral body may be equally shared on or over the entire outer surface of the artificial disc 300. This may reduce the risk for damage or injury to the attached vertebral bodies and/or the artificial disc 300 itself.

The superior insert 314 may include a mating sphere 315, and the inferior insert 324 may include a larger, spherical mating socket 325. The mating sphere 315 may have a radius that is smaller than the radius of the socket 325. This arrangement may enable rolling articulation between the sphere 315 and the socket 325. By extension, the endplates 310, 320 may have a rolling articulation, giving the artificial disc 300 a more natural range of motion. For example, the endplates 310, 320 may roll laterally to permit lateral bending, and they may roll along an anterior/posterior axis to enable flexion and extension. In addition, the superior endplate 310 may rotate relative to the inferior endplate 320, or vice versa, to allow axial rotation. The superior insert 314 and the inferior insert 324 may be made from PEEK or any like material.

Figure 8:
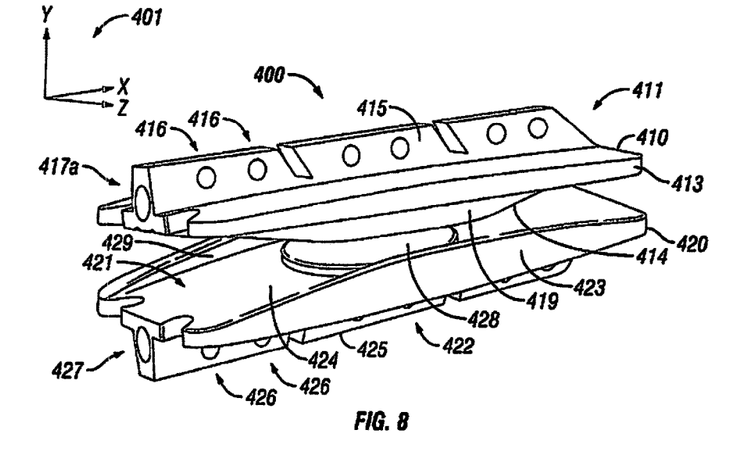
FIG. 8 shows an artificial disc, according to a still further aspect of the disclosure.

FIG. 8 shows an artificial disc 400 that is constructed according to an additional aspect of the disclosure. Axes 401 may represent the three-dimensional orientation of the artificial disc 400. For example, the axis marked X may be approximately aligned with or parallel to an medial/lateral axis of the disc 400. The Y axis may be roughly parallel to a superior/inferior axis of the disc 400. The Z axis may be approximately parallel to an anterior/posterior axis of the artificial disc 400.

The artificial disc 400 may include a superior endplate 410 and an inferior endplate 420. The superior endplate 410 may have a superior surface 411 and an inferior surface 412. The superior surface 411 may include one or more serrated keels 415. Each keel 415 may have a longitudinal axis that is approximately parallel to a medial/lateral axis of the disc 400. Each keel 415 may also have one or more holes 416 that are substantially perpendicular to the longitudinal axis of the keel. For example, the holes 416 may be roughly parallel to a anterior/posterior axis of the disc 400. The holes 416 may encourage bony in-growth, thereby strengthening the attachment or interface between the endplate 410 and the underlying vertebral body or other bone (not shown). The superior endplate 410 may include a lateral socket 417a for receiving a tool or holder (not shown) for gripping the artificial disc 400 during a surgical procedure.

Figure 9:
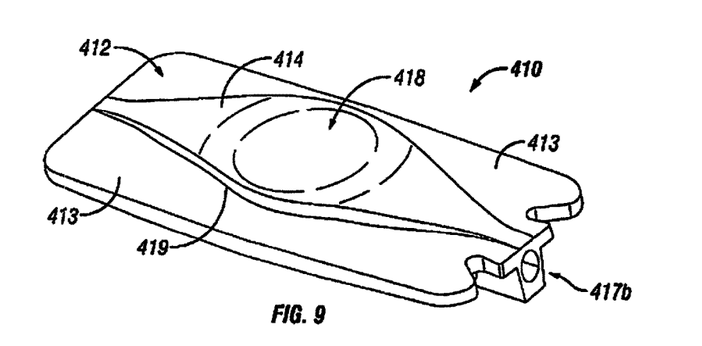
FIG. 9 shows the superior surface of the inferior endplate of the artificial disc of FIG. 8.

FIG. 9 shows the inferior surface 412 of the endplate 410. The inferior surface 412 may be divided into two side regions 413 that are separated by a center region 414. The cross-sectional thickness of the endplate 410 may be thinner in the side regions 413 and thicker in the center region 414. The center region 414 and the side regions 413 may be separated by a lip 419. The center region 414 may include a socket 418 having a concave spherical or rounded shape.

FIG. 9 also shows a lateral socket 417b for receiving a tool or holder (not shown) for use in surgery. Traditionally, an intervertebral disc, which is anterior of the spinal cord, is accessed from the patient's anterior. For procedures in the lumbar region of the spine, the surgeon must cut and navigate through the muscles, tissues, and organs of the patient's abdomen. In contrast, a posterior procedure accesses the disc from an incision on the patient's back, and a transforaminal procedure accesses the disc from an incision made to one side of the spine. In certain cases, the lumbar region of the spine may also be accessed from a direct lateral approach through the patient's side. These procedures may be easier for a surgeon to perform. In addition, these procedures may cause less trauma to the patient and result in faster recovery.

The inferior endplate 420 may have a superior surface 421 and an inferior surface 422. The superior surface 421 may be divided into two side regions 423 and a center region 424. The cross-sectional thickness of the endplate 420 may be thicker in the side regions 423 and thinner in the center region 424. This arrangement may be the opposite or inverse of the superior endplate 410. The superior surface 421 may further include a mating sphere 428, which may mate with the socket 418 of the superior endplate 410 when the artificial disc 400 is fully assembled, as shown in FIG. 8. The inferior endplate 420 may have an inferior surface 422 with one or more serrated keels 425. The keel 425 may have a longitudinal axis that is approximately parallel to medial/lateral axis of the disc 400. The keel 425 may include one or more holes 426 that are substantially perpendicular to the longitudinal axis of the keel. For example, the holes 426 may be roughly parallel to a anterior/posterior axis of the disc 400. The holes 426 may encourage bony in-growth, thereby strengthening the attachment or interface between the endplate 420 and the underlying vertebral body or other bone (not shown). The inferior endplate 420 may additionally include a lateral socket 427 for receiving a tool or holder (not shown) for gripping the artificial disc 400 during a surgical procedure. The inferior endplate 420 may likewise have an opposite lateral socket (not shown) for receiving a tool for gripping the disc 400.

The inferior endplate 420 may include a mating sphere 428, and the superior endplate 410 may include a larger, spherical mating socket 418. The mating sphere 428 may have a radius that is smaller than the radius of socket 418. This arrangement may enable roll/slide articulation between sphere 428 and socket 418. By extension, the endplates 410, 420 may have a roll/slide articulation, giving the artificial disc 400 a more natural range of motion. In particular, the endplates 410, 420 may roll laterally to permit lateral bending, and they may roll along an anterior/posterior axis to enable flexion and extension. In addition, the superior endplate 410 may rotate relative to the inferior endplate 420, or vice versa, to allow axial rotation.

The superior center region 414 may interact with the inferior side regions 423 to limit axial rotation. When the superior endplate 410 is rotated relative to the inferior endplate 420, the lip 419 may be brought into contact with the lip 429. This contact may prevent further rotation of endplate 410. The dimensions of the center regions 414, 424; the side regions 413, 423; and the lips 419, 429 may be selected so as to select a particular range of motion for a particular application of the disc 400. For example, a replacement disc for an intervertebral disc at the top of the thoracic spine may require a different range of motion than a replacement disc for the bottom for the thoracic spine.

The superior endplate 410 and the inferior endplate 420 may be made from metal, such as, e.g., stainless steel, titanium, Co—Cr—Mo alloy or the like; ceramic; PEEK; or any other hard material suitable for bearing contact, as will be understood by one skilled in the art. Surfaces of the artificial disc 400 that will contact bone, such as the superior surface 411 and inferior surface 422, may be treated with a titanium and/or hydroxyapatite plasma spray coating to encourage bony on-growth. The bony on-growth may act to strengthen the attachment or interface between the artificial disc 400 and the underlying vertebrae.

Figure 10:
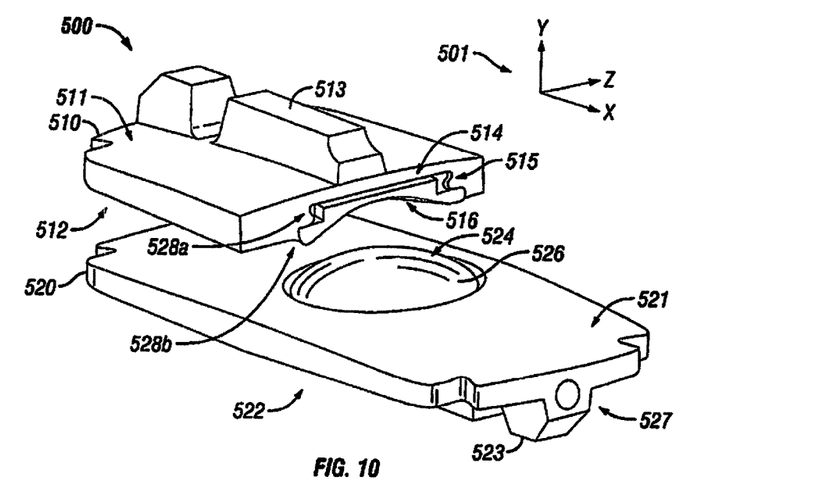
FIG. 10 shows an artificial disc, according to an additional aspect of the disclosure.

FIG. 10 shows an artificial disc 500 according to an additional aspect of the disclosure. Axes 501 may represent the three-dimensional orientation of the artificial disc 500. For example, the axis marked X may be approximately aligned with or parallel to an medial/lateral axis of the disc 500. The Y axis may be roughly parallel to a superior/inferior axis of the disc 500. The Z axis may be approximately parallel to an anterior/posterior axis of the artificial disc 500.

The artificial disc 500 may include a superior endplate 510 and an inferior endplate 520. The superior endplate 510 may have a superior surface 511 and an inferior surface 512. One or more serrated keels 513 may be positioned on the superior surface 511. Each keel 513 may have a longitudinal axis that is approximately parallel to an medial/lateral axis of disc 500. The keel 513 may have one or more holes (not shown) that are substantially perpendicular to the longitudinal axis of the keel, and these holes may serve to encourage bony in-growth from the supporting vertebral body or other bone (not shown). Bony in-growth may strengthen the attachment of the endplate 510 to the vertebral body or other bone. The superior surface 511 may be bi-convex, a shape that may be complementary to a vertebral body or other bone and may provide for an anatomical fit between the surface 511 and the vertebral body (not shown).

The inferior surface 512 may be convex along an medial/lateral axis of the artificial disc 500, or it may be bi-convex. The inferior surface 512 may include a socket 514 for an insert 516. The socket 514 may have a circular wall 528 that is divided into a superior portion 528a and an inferior portion 528b by a lip 515. The inferior portion 528b, which may be closer to the inferior surface 512, may have a larger diameter than the superior portion 528a of the wall 528.

The inferior endplate 520 may include a superior surface 521 and an inferior surface 522. One or more serrated keels 523 may be located on the inferior surface 522. The keel 523 may have a longitudinal axis that is roughly parallel to a medial/lateral axis of the disc 500. The keel 523 may have one or more holes (not shown) that are substantially perpendicular to the longitudinal axis of the keel 523. The holes may function to encourage bony in-growth from an underlying bone, such as an endplate of a vertebral body. The inferior surface 522 may be bi-convex and may have a shape that is complementary to an attached underlying bone, providing an anatomical fit between the surface 522 and the vertebral body (not shown).

Similarly, the superior surface 521 of the inferior endplate 520 may have a shape that is bi-convex, or it may be convex only along a medial/lateral axis of the disc 500. The superior surface may also include a socket 524 for receiving an insert 526. The socket 524 may have an internal design that is similar or identical to the socket 514 of the superior endplate 510. For example, the socket 524 may have a circular side wall that is divided into superior and inferior portions by a lip (not shown). The superior portion may have a wider diameter than the lower portion. Additionally, the inferior endplate 520 may have a socket 527 for receiving a tool (not shown) to grip or hold the artificial disc 500 during surgery. While the socket 527 is shown only on the lateral end of the superior plate, one skilled in the art will appreciate that identical sockets may be located on superior endplate 510, as well as at the opposite end of both endplates 510, 520.

Figure 11:
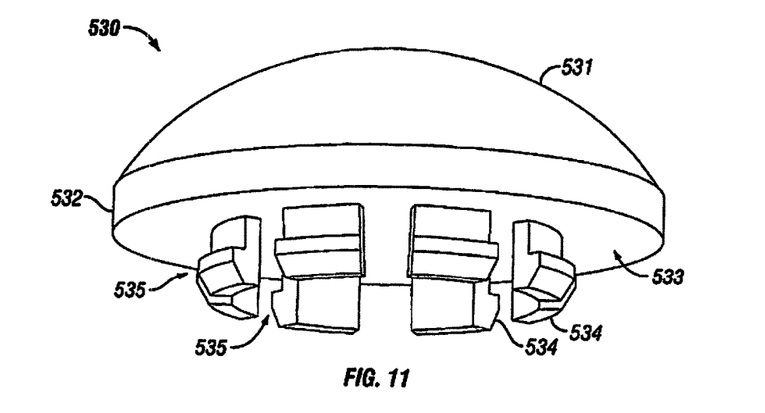
FIG. 11 shows an exemplary insert that may be used with the endplates of FIG. 10.

FIG. 11 shows an example of an insert 526 for use with the superior endplate 510 or inferior endplate 520. The insert 530 may be designed to snap or fit into socket 514 or socket 524. The insert 530 may include an upper surface 531, a side 532, and a lower surface 533. The upper surface 531 may be contiguous with an inferior surface 512 of a superior endplate 510, or it may be contiguous with a superior surface 521 of an inferior endplate 510. The side 532 and the lower surface 533 may be placed within the socket 514, 524. One or more tabs 534 may extend from the lower surface 533. The tab 533 may include a hook 535 for securing the insert 503 in a socket 514, 524. The tab 534 may have a thin cross-section at its base where it attaches to the surface 533. The cross-section may become thicker at the hook and then taper to a point or flat tip at the end of the tab 534 that is farthest from surface 533. The design of the tabs 534 may allow the insert 530 to be easily attached to a socket 514, 524 but prevent easy removal. For example, the side 532 of the insert 530 may abut the inferior sidewall 528b when the insert 530 is placed into socket 514. The narrow base portion of tab 534 may be placed against the lip 515, and the hook portion 535 of the tab 534 may press against the superior sidewall 528a. In this arrangement, the hooks 535 may be complementary to the shape of the lip 515 and the sidewall 528a. The hooks 535 may grip the lip 515, thereby preventing the insert 530 from leaving the socket.

While the insert 530 is shown with an upper surface 531 that has a domed or spherical shape, other arrangements and structures are contemplated and may be used without departing from the spirit or scope of the disclosure, including the attached claims and drawings. For example, the, upper surface 531 may have a concave rounded or spherical shape, such as the insert 516, shown in FIG. 10. Such a shape may be used to mate with the spherical insert 526, also shown in FIG. 10. Another possible arrangement is the use of two spherical inserts for a sphere-on-sphere arrangement.

The first arrangement, with a smaller sphere in a larger spherical socket, may enable roll/slide articulation between the sphere 526 and the socket. By extension, the endplates 510, 520 may have a roll/slide articulation, giving the artificial disc 500 a more natural range of motion. For example, the endplates 510, 520 may roll laterally to permit lateral bending, and they may roll along a medial/lateral axis to enable flexion and extension. In addition, the superior endplate 510 may rotate relative to the inferior endplate 520, or vice versa, to allow axial rotation.

In the second arrangement, which may be sphere-on-sphere, the contact area between the endplates 510, 520 may be minimal. This arrangement may allow the endplates 510, 520 to articulate against each other in a roll/slide manner. For example, the endplates 510, 520 may roll laterally to permit lateral bending, and they may roll along a medial/lateral axis to enable flexion and extension. In addition, the superior endplate 510 may rotate relative to the inferior endplate 520, or vice versa, to allow axial rotation.

The superior endplate 510 and the inferior endplate 520 may be made from metal, such as, e.g., stainless steel, titanium, Co—Cr—Mo alloy, or the like; ceramic; or any other hard material suitable for bearing contact, as will be understood by one skilled in the art. The Inserts 516, 526, 530 may be made from PEEK or any other suitable material, as will be understood by one skilled in the art. The surfaces of the artificial disc 500 that may contact bone, such as the superior surface 511 and inferior surface 522, may be treated with a titanium and/or hydroxyapatite plasma spray coating to encourage bony on-growth. The bony on-growth may act to strengthen the attachment or interface between the artificial disc 500 and the underlying vertebrae.

While the disclosure has been described in terms of exemplary embodiments, those skilled in the art will recognize that the disclosure can be practiced with modifications in the spirit and scope of the appended claims. These examples given above are merely illustrative and are not meant to be an exhaustive list of all possible designs, embodiments, applications or modifications of the disclosure.

What is claimed is:

1. An artificial disc comprising:
a superior endplate having a superior surface, an inferior surface, a first end, a second end, a first side and a second side, the first side extending from the first end to the second end and the second side extending from the first end to the second end;
an inferior endplate having a superior surface and an inferior surface;
wherein the inferior surface of the superior endplate includes two side regions separated by a center region;
wherein the superior surface of the inferior endplate includes two side regions and a center region;
wherein the center region of the superior endplate includes a socket having a concave spherical shape, wherein the superior surface of the inferior endplate includes a mating sphere that mates with the socket of the superior endplate, wherein the mating sphere has a radius that is smaller than a radius of the socket,
wherein the superior endplate contains a first lip separating one of the two side regions from the center region and extending from the first end to the second end of the superior endplate such that the first lip extends along an entire length of the superior endplate,
wherein the inferior endplate contains a second lip and wherein the first lip and the second lip contact when the superior endplate is rotated relative to the inferior endplate,
wherein the superior endplate comprises a keel extending from the first end to the second end, and
wherein the inferior endplate comprises a keel extending from the first end to the second end, and
wherein the keel of the superior endplate and the keel of the inferior endplate includes a lateral socket for receiving a tool,
wherein the distance between the first end and the second end is greater than the distance between the first side and the second side.

2. The artificial disc of claim 1, wherein the center region and the other of the two side regions of the superior endplate are separated by a third lip.

3. The artificial disc of claim 2, wherein the inferior endplate contains a fourth lip configured to contact the third lip of the superior endplate.

4. The artificial disc of claim 1, wherein the cross sectional thickness of the superior endplate is thinner in the side regions and thicker in the center region.

5. The artificial disc of claim 4, wherein the cross sectional thickness of the inferior endplate is thicker in the side regions and thinner in the center region.

6. The artificial disc of claim 1, wherein the first and second keels include one or more holes that are substantially perpendicular to the longitudinal axis of the keel.

7. The artificial disc of claim 1, wherein mating of the socket and the mating sphere configured provide roll/slide articulation to permit lateral bending and flexion and extension.

8. The artificial disc of claim 1, wherein mating of the socket and the mating sphere configured provide roll/slide articulation to permit lateral bending and flexion and extension.

9. The artificial disc of claim 1, wherein the third lip extends from the first end to the second end of the superior endplate.

10. An artificial disc comprising:
a superior endplate having a superior surface, an inferior surface, a first end, a second end, a first side and a second side, the first side extending from the first end to the second end and the second side extending from the first end to the second end;
an inferior endplate having a superior surface and an inferior surface;
wherein the inferior surface of the superior endplate includes a two side regions separated by a center region,
wherein the superior surface of the inferior endplate includes two side regions and a center region,
wherein the center region of the superior endplate includes a socket having a concave spherical shape,
wherein the superior surface of the inferior endplate includes a mating sphere that mates with the socket of the superior endplate, wherein the mating sphere has a radius that is smaller than a radius of the socket,
wherein the center region and the side regions of the superior endplate are separated by a first lip extending from the first end to the second end of the superior endplate such that the first lip extends along an entire length of the superior endplate,
wherein the superior center region interacts with the inferior side regions to limit rotation via the first lip contacting a second lip, wherein the second lip is disposed on the superior surface of the inferior endplate, wherein the superior endplate comprises a keel extending from the first end to the second end, and wherein the inferior endplate comprises a keel extending from the first end to the second end, and wherein the keel of the superior endplate and the keel of the inferior endplate includes a lateral socket for receiving a tool, wherein the distance between the first end and the second end is greater than the distance between the first side and the second side.

11. The artificial disc of claim 10, wherein the cross sectional thickness of the superior endplate is thinner in the side regions and thicker in the center region.

12. The artificial disc of claim 11, wherein the cross sectional thickness of the inferior endplate is thicker in the side regions and thinner in the center region.

13. The artificial disc of claim 10, wherein the first and second keels include one or more holes that are substantially perpendicular to the longitudinal axis of the keel.

14. An artificial disc comprising:
a superior endplate having a superior surface, an inferior surface, a first end, a second end, a first side and a second side, the first side extending from the first end to the second end and the second side extending from the first end to the second end;
an inferior endplate having a superior surface and an inferior surface;
wherein the inferior surface of the superior endplate includes a two side regions separated by a center region,
wherein the superior surface of the inferior endplate includes two side regions and a center region,
wherein the center region of the superior endplate includes a socket having a concave spherical shape,
wherein the superior surface of the inferior endplate includes a mating sphere that mates with the socket of the superior endplate, wherein the mating sphere has a radius that is smaller than a radius of the socket,
wherein the center regions separates the side regions of the superior endplate, one of the side regions being separated from the center region by a first lip extending from the first end to the second end of the superior endplate such that the first lip extends along an entire length of the superior endplate,
wherein the superior center region interacts with the inferior side regions to limit rotation via the first lip contacting the second lip, wherein the second lip is disposed on the superior surface of the inferior endplate, wherein the artificial disc is positioned laterally,
wherein the superior endplate comprises a keel extending from the first end to the second end, and
wherein the inferior endplate comprises a keel extending from the first end to the second end, and
wherein the keel of the superior endplate and the keel of the inferior endplate includes a lateral socket for receiving a tool,
wherein the distance between the first end and the second end is greater than the distance between the first side and the second side.

15. The artificial disc of claim 14, wherein the other of the side regions is separated from the center region by a third lip extending from the first end to the second end of the superior endplate.

16. The artificial disc of claim 15, wherein the inferior endplate contains a fourth lip configured to contact the third lip of the superior endplate.

* * * * *